Figure 1:
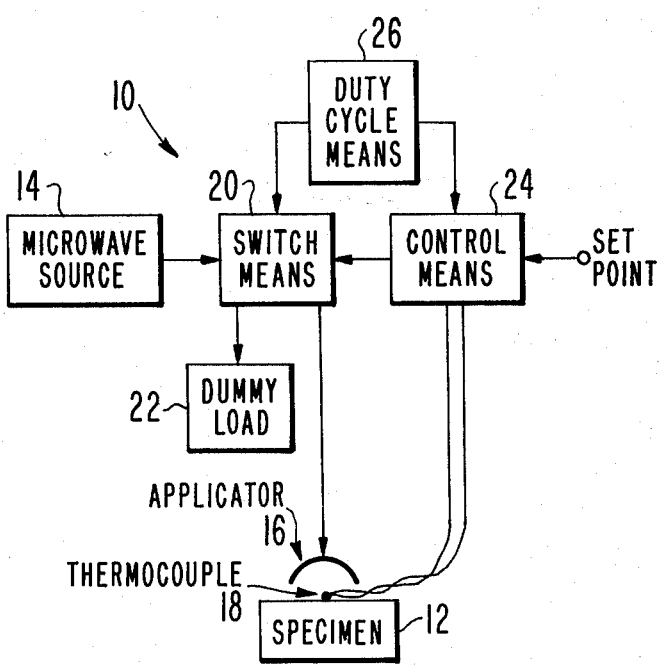

United States Patent [19]

Paglione

[11] 4,228,809

[45] Oct. 21, 1980

[54] TEMPERATURE CONTROLLER FOR A MICROWAVE HEATING SYSTEM

[75] Inventor: Robert W. Paglione, Robbinsville, N.J.

[73] Assignee: RCA Corporation, New York, N.Y.

[21] Appl. No.: 840,036

[22] Filed: Oct. 6, 1977

[51] Int. Cl.³ .............................................. A61N 5/02
[52] U.S. Cl. ............................. 128/804; 219/10.55 B
[58] Field of Search ....... 128/2 A, 399, 404, 412–413, 128/421–422, 736, 804; 219/10.55 B, 10.55 M, 10.55 R

[56] References Cited

U.S. PATENT DOCUMENTS

| | | | |
|---|---|---|---|
| 3,281,568 | 10/1966 | Haagensen | 219/10.55 B |
| 3,569,656 | 3/1971 | White et al. | 219/10.55 B X |
| 3,684,978 | 8/1972 | Otaguro | 219/10.55 B X |
| 3,862,390 | 1/1975 | Noda | 219/10.55 B X |
| 4,002,175 | 1/1977 | Brainard et al. | 128/399 |
| 4,016,886 | 4/1977 | Doss et al. | 128/422 |
| 4,095,602 | 6/1978 | LeVeen | 128/422 X |

FOREIGN PATENT DOCUMENTS 1239789  7/1971  United Kingdom ......... 219/10.55 B X

OTHER PUBLICATIONS

Ely, T. S., "Heating Characteristics of Lab Animals Exposed to 10 Centimeter Microwaves", IEEE Trans. BME, Oct. 1964, p. 123–137.
Dickson, J. A., "Tumor Eradication in the Rabbit by RF Heating", Cancer Research 37, 2162–2169, Jul. 1977.

*Primary Examiner*—Robert W. Michell
*Assistant Examiner*—Francis J. Jaworski
*Attorney, Agent, or Firm*—H. Christoffersen; Samuel Cohen; Robert L. Troike

[57] ABSTRACT

In a microwave system where energy is directed through an applicator to heat a specimen, the inaccuracies encountered when control temperatures are monitored with thermocouples located in the presence of the microwave field are precluded through the use of a duty cycle that segregates the temperature monitoring periods from the periods when the microwave energy is directed through the applicator.

4 Claims, 2 Drawing Figures

TEMPERATURE CONTROLLER FOR A MICROWAVE HEATING SYSTEM

The present invention relates to a temperature controller for use in a system which applies microwave energy through an applicator in heating a specimen to temperatures that are monitored by a thermocouple. In application Ser. No. 808,292, filed June 20, 1977 and assigned to the same assignee as the present invention, a temperature controller for avoiding the use of thermocouples in such systems is disclosed. As discussed in that application regarding such systems for hyperthermia treatment where microwave energy is directed through applicators to heat cancerous tumors, thermocouples have been used in prior art systems and present some disadvantages. By far, the most significant of these disadvantages is due to the metallic nature of thermocouples which causes radiation pick-up to result in monitored temperature inaccuracies.

In the present invention, a switch is disposed to direct the microwave energy through either the applicator or a dummy load and a controller, which is responsive to the specimen temperature, actuates this switch to direct the microwave energy through the applicator when the specimen temperature is below a set point and through the dummy load when the specimen temperature is at or above the set point. A thermocouple is used to monitor the specimen temperature and the inaccuracies normally encountered therefrom are precluded by establishing a duty cycle that performs such monitoring periodically with the switch actuated to direct the microwave energy through the dummy load.

Figure 2:
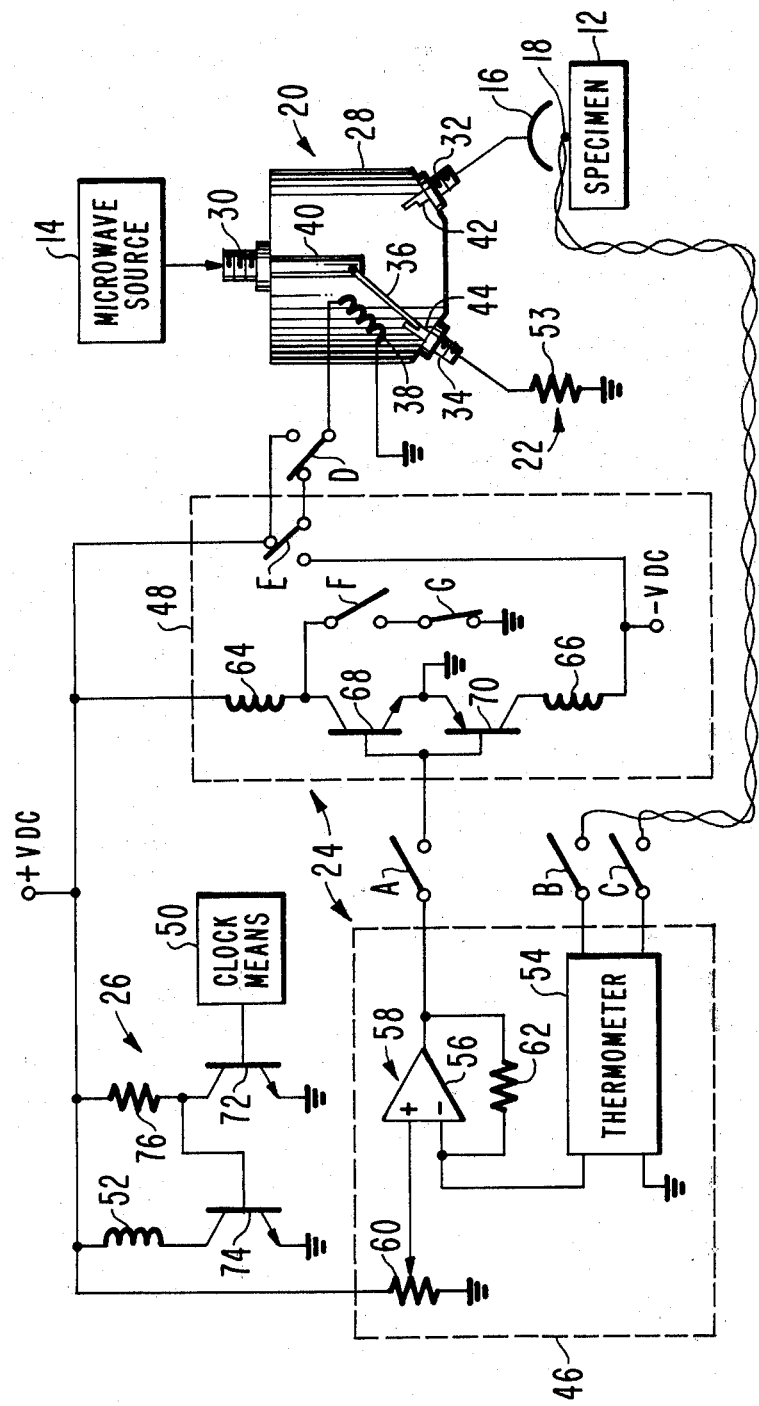

In the drawings:

FIG. 1 is a block diagram of a microwave system with the temperature controller of this invention incorporated therein; and FIG. 2 is a schematic diagram wherein the FIG. 1 block elements that relate to the temperature controller of this invention are further defined in the preferred embodiments thereof.

Turning now to the drawings, the controller of this invention is incorporated in the FIG. 1 block diagram of a system 10 which heats a specimen 12 to controlled temperature levels by directing energy from a microwave source 14 through an applicator 16. In a manner conventional to the prior art, a thermocouple 18 is disposed within the microwave field from the applicator 16 to monitor the temperature of the specimen 12. The controller of this invention regulates the specimen temperature by combining a switch means 20 for directing the microwave energy through either the applicator 16 or a dummy load 22 with a control means 24 for actuating the switch means 20 to direct the microwave energy through the applicator 16 when the specimen temperature is below a set point and through the dummy load 22 when the specimen temperature is at or above the set point. The controller of this invention also includes a duty cycle means 26 for synchronizing the switch means 20 and the control means 24 to periodically monitor the specimen temperature with the microwave energy directed through the dummy load 22. Of course, the leads of the thermocouple 18 connect to the control means 24 which must respond to the temperature of the specimen 12.

By allowing the specimen temperature to be monitored only when the microwave energy is directed through the dummy load 22, the controller of this invention avoids the usual problems that are encountered due to the thermocouple 18 being located in the presence of the microwave field from the applicator 16. This is so because the interferring radiation pick-up caused by the metallic nature of the thermocouple 18 is precluded to assure the accuracy of temperatures monitored therewith.

Although many embodiments of the invention are possible, the preferred embodiments thereof are illustrated in FIG. 2, where a coaxial switch 28 of the type supplied by Hewlett-Packard under part number 8761A is utilized as the switch means 20. This switch 28 includes an input coaxial connector 30 and two output coaxial connectors 32 and 34, along with a flexible reed contact 36 that is magnetically coupled to a winding 38. Each of the coaxial connectors 30, 32 and 34 have center conductors 40, 42 and 44 respectively therethrough and the reed contact 36 is connected at one end to the center conductor 40 of the input connector 30, while the other end thereof is positionable in response to signals passing through the winding 38 to electrically connect with either center conductor 42 or 44 of the output connectors 32 or 34. Those skilled in the art will readily appreciate without further explanation that the switch means 20 could be an electronic arrangement rather than the mechanical arrangement of coaxial switch 28.

The control means 24 in FIG. 2 combines a threshold means 46 for comparing the thermocouple output with the set point to produce an output having either a first polarity when the specimen temperature falls below the set point or a second polarity when the specimen temperature rises to or above the set point, with a latching means 48 for holding the switch means 20 at each output position thereof in response respectively to the outputs of first and second polarities from the threshold means 46. A means 50 for generating a clock pulse and a relay having a plurality of switch contacts A, B, C and D magnetically actuated by a winding 52 are included in the duty cycle means 26. The clock pulse means 50 is connected to energize the relay winding 52 through a transistor switching circuit that will be discussed later in this application. The relay contacts A, B, C and D are all shown in the positions they assume when the winding 52 is not energized by the clock pulse. Contact A is single throw and disposed to disconnect the output of the threshold means 46 from the input of the latching means 48, while contacts B and C are single throw and disposed to disconnect the output of the thermocouple 18 from the input of the threshold means 46. Contact D is double throw and disposed to disable the switch means 20 relative to the latching means 48, while independently enabling it to direct the microwave energy through a resistor 53 which is connected as the dummy load 22.

Operation of the FIG. 2 embodiments is such that throughout each clock pulse of the duty cycle means 26, contacts A, B, C and D all change their positions from those shown. Consequently, the flexible reed contact 36 of the coaxial switch 28 becomes electrically connected to the center conductor 44 of output connector 34 and the microwave energy is thereby directed through the dummy load 22 regardless of what the output condition of the latching means 48. Furthermore, the input and output of the threshold means 46 becomes respectively connected to the leads of the thermocouple 18 and to the input of the latching means 48. Therefore, the specimen temperature is monitored concurrently with the output from the threshold means 46 being connected to set the latching means 48, but only when the microwave energy is directed through the dummy load 22.

Although other arrangements of the threshold means 46 are possible, a voltage proportional to the specimen temperature is derived from the signal of the thermocouple 18 through a thermometer 54 in FIG. 2. This voltage is connected to the inverting input of an operational amplifier 56 which is otherwise arranged as a differential comparator 58. The adjustable output voltage from a potentiometer 60 is connected as the set point to the noninverting input of the operational amplifier 56, while a resistor 62 is connected between the output and the inverting input thereof. The potentiometer 60 is connected between a voltage source having a particular polarity such as a positive DC voltage source and a reference voltage such as ground, so that the set point is adjustable therebetween. Operational amplifier 56 functions to produce an output proportional to the differential existing between voltages of similar polarity on its inverting and noninverting inputs. Therefore, the output of operational amplifier 56 changes polarity when the specimen temperature signal on its inverting input transgresses through the set point signal on its noninverting input. Of course, the resistor 62 could be a large value or deleted altogether to increase the gain of operational amplifier 56 which will then saturate at opposite polarities when the inverting input thereof transgresses through the set point from either side.

Although the latching means 48 could be accomplished with an electronic switching circuit, a pair of magnetic relays are combined therein with a pair of transistors for the embodiments of FIG. 2. One of the relays includes switch contacts E and F which are actuated by a winding 64, while the other includes switch contact G which is actuated by a winding 66. Contact E is of the double throw type while contacts F and G are of the single throw type. Windings 64 and 66 are series-connected through a combination of an NPN transistor 68 and a PNP transistor 70 between voltage sources of opposite polarities, such as the positive DC voltage source and a negative DC voltage source. The transistors 68 and 70 are connected with the bases thereof commonly connected through contact A to the output of the threshold means 46 and the emitters thereof commonly connected to a reference voltage such as ground. The collector of transistor 70 is connected to one end of winding 66, while the collector of transistor 68 is connected to one end of winding 64 and to the reference voltage through series-connected contacts F and G. Output is taken from the latching means 48 at the common terminal of double throw contact E which has the other terminals thereof connected separately to the positive and negative DC voltage sources. Contacts E, F and G are shown in the positions they assume when their actuating windings 64 and 66 are not energized, with contacts F and G being normally open and normally closed, respectively. Although the output from the latching means 48 is periodically disconnected from the winding 38 of coaxial switch 28 through contact D of the duty cycle means 26 when the specimen temperature is being monitored, it is set to the level of either the positive or negative DC voltage source during each monitoring period. As discussed previously, contact A of the duty cycle means 26 is closed during such monitoring periods so when output from the threshold means 46 is positive, the transistor 68 becomes conductive to energize winding 64 which actuates contact F to its closed position and contact E to its negative DC voltage source position. Because winding 64 is then energized through closed contacts F and G, contact E holds the output from the latching means 48 at the level of the negative DC voltage source when the output from the threshold means 46 is disconnected through contact A after each monitoring period. The output from the latching means 48 is only changed thereafter to the level of the positive DC voltage source during some later monitoring period when output from the threshold means 46 is negative to render transistor 70 conductive. When this occurs, winding 66 becomes energized to open contact G and thereby deenergize winding 64 which causes contact F to open and contact E to switch back to the positive DC voltage source.

Although relay winding 52 in the duty cycle means 26 is energized from the positive DC voltage source in the embodiments of FIG. 2, a magnetic relay could have been selected to operate from the negative DC voltage source. Furthermore, the pulse of clock means 50 in duty cycle means 26 could either be high level or low level depending on the nature of the switching circuit utilized to interconnect between the clock means 50 and the winding 52. In the embodiments of FIG. 2, the pulse is low level and two NPN transistors 72 and 74 are arranged in the switching circuit. The clock pulse is connected to the base of transistor 72 which has the emitter thereof connected to ground while the collector thereof is connected to the base of transistor 74 and also to the positive DC voltage source through a resistor 76. The emitter and collector of transistor 74 are also connected to ground and the positive DC voltage source respectively, with the latter being connected through the winding 52. The switching circuit of the duty cycle means 26 operates in response to each low level clock pulse by terminating conduction through transistor 72 which renders transistor 74 conductive to energize winding 52. Of course, those skilled in the art will appreciate without further explanation that a single transistor could be utilized in the switching circuit of the duty cycle means 26 and for either a low level or high level clock pulse.

Of course, winding 38 in the coaxial switch 28 presents an inductive load which causes deterioration to relay contacts such as those utilized in the control means 24 of the FIG. 2 embodiments. Such deterioration can be readily avoided by connecting the common terminal of relay contact D to the winding 38 through a bipolar emitter-follower transistor combination. An NPN transistor and a PNP transistor would be connected in such a combination with the bases thereof commonly connected to contact D and the emitters thereof commonly connected to winding 38. The collector of the NPN transistor would be connected to the positive DC voltage source while the collector of the PNP transistor would be connected to the negative DC voltage source. Consequently, winding 38 would be switched to the same polarity voltage source through the bipolar emitter-follower as that to which contact D is connected but without sustaining any arcing from the inductive load. It should also be understood that all connections to the positive and negative DC voltage sources would be made through resistor-capacitor combinations for purposes of decoupling, as is well-known in the electronic arts.

Although this invention has been disclosed herein by describing only a few embodiments thereof, it should be understood by those skilled in the art that numerous changes in the details of construction and the combination or arrangement of parts could be made in the described embodiments without departure from the true scope and spirit of the invention. Therefore, the present disclosure should be construed as illustrative rather than limiting.

What is claimed is:

1. In a microwave system of the type wherein a specimen is heated to a controlled temperature level by directing energy through an applicator and detecting the specimen temperature, the improvement comprising:

a dummy load;

a temperature sensing device responsive to the temperature of the specimen for providing a temperature signal indicative of specimen temperature;

switch means for directing the microwave energy through either said applicator or said dummy load, said switch means including an input coaxial connector and two output coaxial connectors along with a flexible magnetic reed contact and a winding disposed to be magnetically coupled thereto, each of said coaxial connectors having a center conductor, said reed contact being connected at one end to the center conductor of said input connector while having the other end thereof positionable to electrically connect with either center conductor of said output connectors in response to signals passing through said winding;

control means responsive to the temperature signal for actuating said switch means to direct the microwave energy through said applicator when the specimen temperature is below a set point and through said dummy load when the specimen temperature is at or above said set point, said control means being connected to receive the temperature signal from the temperature sensing device, said control means including threshold means for comparing the temperature signal from the temperature sensing device with said set point to produce an output having a first polarity when the specimen temperature is below said set point and a second polarity when the specimen temperature is above said set point and latching means for holding said switch means winding across sources of opposite polarity respectively in response to said first or second polarity of said threshold means output, said switch means directing the microwave energy through either the applicator or said dummy load respectively in response to each source of polarity; and duty cycle means for synchronizing said switch means and said control means to apply the temperature signal to the threshold means only when the microwave energy is directed through said dummy load;

said duty cycle means including clock means for generating a periodic pulse and a relay having a plurality of switch contacts magnetically activated by a winding, said clock means being connected across said relay winding and said switch contacts being disposed to disable said switch means winding relative to said latching means while independently enabling it relative to said source polarity that energizes said switch means winding to direct the microwave energy through said dummy load and to connect the input and output of said threshold means to the temperature sensing device output and said latching means input respectively, when said clock pulse occurs.

2. The microwave system of claim 1 wherein said threshold means includes an operational amplifier having the inverting and noninverting inputs thereof separately connected to the temperature sensing device output and to said set point respectively, and the output therefrom connected to the inverting input thereof through a first resistor; and output from said operational amplifier being connected to the input of said latching means and being the algebraic difference between the temperature sensing device output and said set point.

3. In a microwave system of the type wherein a specimen is heated to a controlled temperature level by directing energy through an applicator and detecting the specimen temperature, the improvement comprising:

a dummy load;

a temperature sensing device responsive to the temperature of the specimen for providing a temperature signal indicative of specimen temperature;

switch means for directing the microwave energy through either said applicator or said dummy load;

said switch means including an input coaxial connector and two output coaxial connectors along with a flexible magnetic reed contact and a winding disposed to be magnetically coupled thereto, each of said coaxial connectors having a center conductor, said reed contact being connected at one end to the center conductor of said input connector while having the other end thereof positionable to electrically connect with either center conductor of said output connectors in response to signals passing through said winding;

control means responsive to the temperature signal for actuating said switch means to direct the microwave energy through said applicator when the specimen temperature is below a set point and through said dummy load when the specimen temperature is at or above said set point, said control means being connected to receive the temperature signal from the temperature sensing device;

said control means including threshold means for comparing the temperature signal from the temperature sensing device with said set point to produce an output having a first polarity when the specimen temperature is below said set point and a second polarity when the specimen temperature is above said set point, and latching means for holding said switch means winding across sources of opposite polarity respectively in response to said first or second polarity of said threshold means output, said switch means directing the microwave energy through either the applicator or said dummy load respectively in response to each source of polarity;

said latching means including first and second magnetic relays;

said first relay having a single throw contact and a double throw contact actuated by a first winding, said second relay having a single throw contact actuated by a second winding, said first winding being series connected to said second winding through a combination of a NPN transistor and a PNP transistor between voltage sources of opposite polarities, said single throw contacts of said first and second relays being normally opened and normally closed respectively, and being series connected between the connection of said first winding with said transistor combination and a voltage reference of intermediate value to said opposite polarity sources, said double throw contact of said first relay being disposed to connect each of said opposite polarity sources respectively across said switch means winding in response to said first or second polarity of said threshold means output, said transistors in combination having the bases thereof commonly connected to said threshold means output and the emitters thereof commonly connected to said reference voltage with the collectors of said NPN and PNP transistors being connected respectively to said first and second relay windings, said first relay winding becoming conductively latched through said single throw contacts of said first and second relays while said switch means winding is connected across said source of polarity through said double throw contact of said first relay to direct the microwave energy through the applicator when said NPN transistor is rendered conductive by positive output from said threshold means, said second relay winding becoming conductive through said PNP transistor to open said single throw contact of said second relay and thereby terminate conduction through said first relay winding when said threshold means output is negative; and duty cycle means for synchronizing said switch means and said control means to apply the temperature signal to the threshold means only when the microwave signal is directed through said dummy load.

4. The microwave system of claim 3 wherein said duty cycle means includes clock means for generating a clock pulse and a third magnetic relay having a double throw contact and first, second and third single throw normally opened contacts actuated by a third winding, said double throw contact of said third relay being disposed to connect the common terminal of said first relay double throw contact, said first and second single throw contacts of said third relay each being connected to interrupt conductively between said temperature sensing device and said threshold means, said third single throw contact of said third relay being connected to interrupt conductively between said threshold means output and said latching means input, said clock means being connected across said third relay winding to actuate said third relay contacts in connecting said threshold means to the temperature sensing device output through said first and second contacts of said third relay and connecting said threshold means output to the latching means input through said third contact of said third relay, while said double throw contact of said third relay disconnects said switch means winding from said first relay double throw contact and connects said switch means winding across said source of polarity that energizes said switch means winding to direct the microwave energy through said dummy load.

* * * * *